United States Patent
Müller et al.

(10) Patent No.: US 6,562,833 B1
(45) Date of Patent: May 13, 2003

(54) USE OF 2-(N-PHENYLAMINO)PYRIMIDINES AS FUNGICIDES, AND NOVEL 2-(N-PHENYLAMINO) PYRIMIDINES

(75) Inventors: Bernd Müller, Frankenthal (DE); Hubert Sauter, Mannheim (DE); Herbert Bayer, Mannheim (DE); Oliver Cullmann, Mannheim (DE); Markus Gewehr, Kastellaun (DE); Wassilios Grammenos, Ludwigshafen (DE); Andreas Gypser, Mannheim (DE); Arne Ptock, Ludwigshafen (DE); Norbert Götz, Worms (DE); Thomas Grote, Schifferstadt (DE); Michael Rack, Heidelberg (DE); Eberhard Ammermann, Heppenheim (DE); Gisela Lorenz, Neustadt (DE); Siegfried Strathmann, Limburgerhof (DE); John-Bryan Speakman, Bobenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/701,859

(22) PCT Filed: May 29, 1999

(86) PCT No.: PCT/EP99/03751
§ 371 (c)(1),
(2), (4) Date: Dec. 5, 2000

(87) PCT Pub. No.: WO99/63821
PCT Pub. Date: Dec. 16, 1999

(30) Foreign Application Priority Data

Jun. 10, 1998 (DE) .......................... 198 25 803

(51) Int. Cl.⁷ .......................... C07D 239/42; A01N 43/54
(52) U.S. Cl. .......................... 514/275; 544/330; 544/332
(58) Field of Search .......................... 514/275; 544/330, 544/332

(56) References Cited

U.S. PATENT DOCUMENTS

| | | | |
|---|---|---|---|
| 4,694,009 A | 9/1987 | Hubele | 514/269 |
| 4,931,560 A | 6/1990 | Hubele | 544/315 |
| 4,973,690 A | 11/1990 | Rempfler | 544/279 |
| 5,439,912 A | 8/1995 | Hubele | 514/275 |

FOREIGN PATENT DOCUMENTS

| | | |
|---|---|---|
| EP | 172 786 | 2/1986 |
| EP | 224 339 | 6/1987 |
| EP | 270 111 | 6/1988 |
| EP | 310 550 | 4/1989 |
| EP | 337 944 | 10/1989 |
| EP | 457 726 | 11/1991 |
| JP | 3-271278 | 12/1991 |
| WO | 97/19065 | 5/1997 |

OTHER PUBLICATIONS

Kreutzberger et al., Antidiabetic Hormones. III. 4,5,6–trisubstituted–2–(4–toluidino)pyrimidine, Journal of Heterocyclic Chemistry, vol. 21, No. 6, pp. 1639–1640, Nov. 1984.*
Falch et al., Chemical Abstract No. 69:59179t, Oct. 1968.*
Derwent DD 151–404, Franke, 1980.
Abst. 3271 278, 1990.

* cited by examiner

Primary Examiner—Deepak Rao
(74) Attorney, Agent, or Firm—Keil & Weinkauf

(57) ABSTRACT

2-(N-phenylamino)pyrimidines of the formula I,

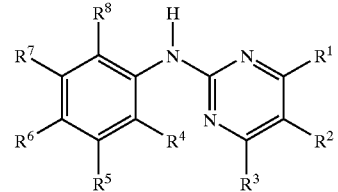

where:

$R^1$, $R^3$ independently of one another are cyano, $C_1$–$C_8$-alkyl, $C_2$–$C_6$-alkenyl, $C_2$–$C_6$-alkynyl, where the radicals alkyl, alkenyl and alkynyl may be substituted by cyano, halogen, $C_1$–$C_4$-alkoxy or $C_1$–$C_4$-alkoxycarbonyl, or are $C_3$–$C_8$-cycloalkyl or a group $C(=NOR^x)R^y$ $R^2$ is halogen, $C_1$–$C_8$-alkyl, $C_2$–$C_6$-alkenyl, $C_2$–$C_6$-alkynyl, where the radicals alkyl, alkenyl and alkynyl may be substituted by cyano, halogen, $C_1$–$C_4$-alkoxy or $C_1$–$C_4$-alkoxycarbonyl, or $R^1$ and $R^2$ together with the two linking carbon atoms form a fused-on partially unsaturated 4- to 8-membered ring which may be up to trisubstituted by identical or different substituents selected from the group consisting of $C_1$–$C_4$-alkyl, halogen and $C_1$–$C_4$-alkoxycarbonyl, which may contain a carbonyl group and/or, in addition to the multiple bond of the pyrimidine ring, a double bond and/or which may be interrupted by O, S or N—($C_1$–$C_4$-alkyl);

the substituents $R^4$ to $R^8$, $R^x$, $R^y$, $R^a$ and $R^b$ are as defined in the description;

are used as fungicides.

7 Claims, No Drawings

USE OF 2-(N-PHENYLAMINO)PYRIMIDINES AS FUNGICIDES, AND NOVEL 2-(N-PHENYLAMINO) PYRIMIDINES

The present invention relates to the use of 2-(N-phenylamino)pyrimidines of the formula I,

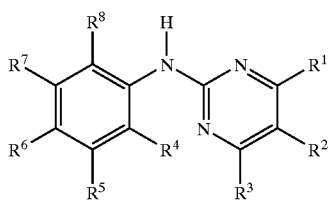

where:
- $R^1$, $R^3$ independently of one another are cyano, $C_1$–$C_8$-alkyl, $C_2$–$C_6$-alkenyl, $C_2$–$C_6$-alkynyl, where the radicals alkyl, alkenyl and alkynyl may be substituted by cyano, halogen, $C_1$–$C_4$-alkoxy or $C_1$–$C_4$-alkoxycarbonyl, or are $C_3$–$C_8$-cycloalkyl or a group $C(=NOR^x)R^y$;
- $R^x$ is hydrogen, $C_1$–$C_8$-alkyl, $C_2$–$C_6$-alkenyl, $C_2$–$C_6$-alkynyl, where the radicals alkyl, alkenyl and alkynyl may be substituted by cyano, halogen, $C_1$–$C_4$-alkoxy or phenyl;
- $R^y$ is hydrogen, $C_1$–$C_8$-alkyl, $C_2$–$C_6$-alkenyl, $C_2$–$C_6$-alkynyl, where the radicals alkyl, alkenyl and alkynyl may be substituted by cyano, halogen or $C_1$–$C_4$-alkoxy;
- $R^2$ is halogen, $C_1$–$C_8$-alkyl, $C_2$–$C_6$-alkenyl, $C_2$–$C_6$-alkynyl, where the radicals alkyl, alkenyl and alkynyl may be substituted by cyano, halogen, $C_1$–$C_4$-alkoxy or $C_1$–$C_4$-alkoxycarbonyl; or
- $R^1$ and $R^2$ together with the two linking carbon atoms form a fused-on partially unsaturated 4- to 8-membered ring which may be up to trisubstituted by identical or different substituents selected from the group consisting of $C_1$–$C_4$-alkyl, halogen and $C_1$–$C_4$-alkoxycarbonyl, which may contain a carbonyl group and/or, in addition to the multiple bond of the pyrimidine ring, a double bond and/or which may be interrupted by O, S or N—($C_1$–$C_4$-alkyl);
- $R^4$ to $R^8$ independently of one another are hydrogen, cyano, halogen, $R^a$, $R^aO$, $R^aS(O)_m$, $R^aO$—(C=O), $R^a$(C=O), $R^aR^bN$—(C=O), $R^aHN$—(C=O), $H_2N$—(C=O), $R^a$—(C=O)—NH, $R^a$—(C=O)—$NR^b$ or $R^aO$—N=C($R^b$);
- $R^a$, $R^b$ are $C_1$–$C_4$-alkyl, $C_3$–$C_6$-alkenyl or $C_3$–$C_6$-alkynyl, each of which may be substituted by cyano, halogen, $C_1$–$C_4$-alkoxy, $C_1$–$C_4$-alkoxycarbonyl or phenyl, or are phenyl which may carry one to three substituents selected from the group consisting of halogen and $C_1$–$C_4$-alkyl;
- m is 0, 1 or 2;

as fungicides.

Fungicidal 2-(N-phenylamino)pyrimidines carrying a hydrogen atom in the 5-position of the pyrimidine ring are known from EP-A 224 339, EP-A 270 111, EP-A 310 550, EP-A 457 726, DD 151404 and JP 03/271278.

2-(N-phenylamino)pyrimidines substituted in the 5-position have been described as intermediates for herbicidally active compounds (EP-A 337 944) and as pharmaceutics (WO-A 97/19065).

Finally, fungicidal 2-(N-phenylamino)pyrimidines which may be substituted in the 5-position and which carry a specific 2-nitrophenyl radical at the amino function are known from EP-A 172 786.

However, the compounds mentioned in EP-A 172 786 do not always fully meet the requirements which have to be met by active compounds in practice.

It is an object of the present invention to provide fungicidally active compounds having improved properties.

We have found that this object is achieved by the above-mentioned compounds, some of which have already been mentioned in the publications EP-A 337 944 and WO-A 97/19065, which are outstandingly suitable for controlling harmful fungi. In addition, we have found novel 2-(N-phenylamino)pyrimidines having improved fungicidal activity.

It is a common feature of all aminopyrimidines according to the invention, both the novel aminopyrimidines and those known from EP-A 337 944 and WO-A 97/19065, that they carry hydrophobic substituents in each of positions 4, 5 and 6.

The novel 2-(N-phenylamino)pyrimidines can be prepared similarly to methods known from the literature. Particularly suitable are the process routes shown in Schemes 1 and 2.

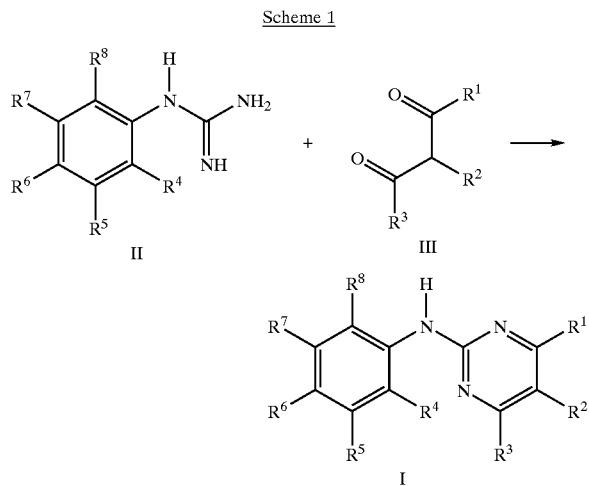

The condensation reaction of the guanidines II with 1,3-dicarbonyl compounds of the formula III to give the 2-(N-phenylamino)pyrimidines I can be carried out as described in EP-A 337 944 and the literature cited therein.

With regard to the synthesis of the guanidines II, reference is made to Houben-Weyl, Methoden der Organischen Chemie, Stuttgart, Vol. VIII pp. 98, 180 to 189. The 1,3-diketones III can be prepared, for example, either by a) Claisen condensation or by b) alkylation or halogenation of a 1,3-diketone which is unsubstituted in the 2-position (Organikum, 1993 Barth Verlagsgesellschaft Leipzig, a) p.487 b) p. 536).

Scheme 2

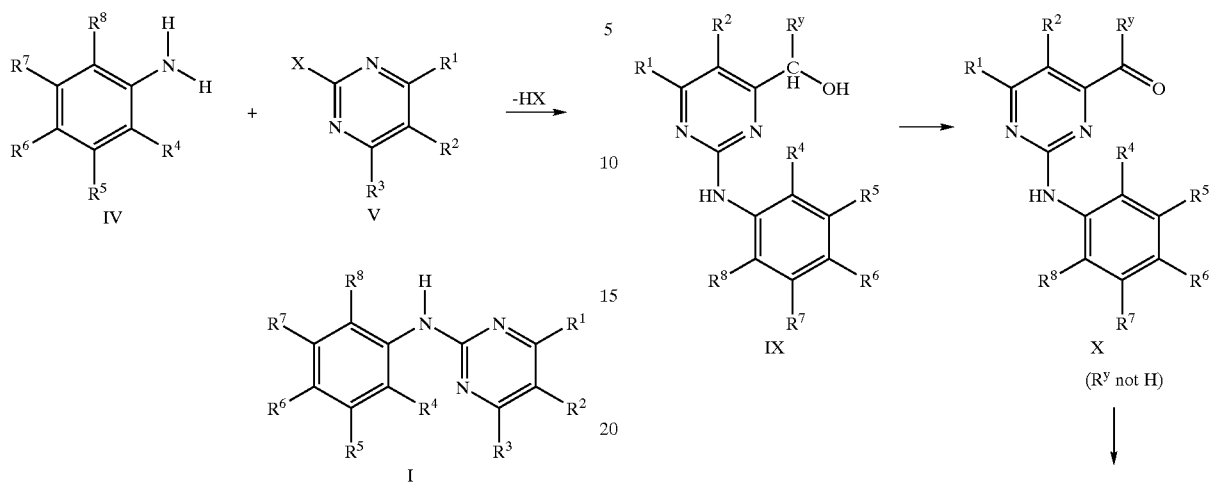

The preparation of the 2-(N-phenylamino)pyrimidines I starting from aniline derivatives of the formula IV and pyrimidine derivatives of the formula V where X is a nucleophilically replaceable group, such as halogen or $C_1$–$C_4$-alkylsulfonyl, is described in EP-A 337 944.

The compounds I according to the invention in which $R^3$ is C(=NOR$^x$)R$^y$ are preferably prepared from the aldehydes VI (see Scheme 3), and the aldehydes VI for their part can be synthesized similarly to EP-A 457 726.

Compounds Ia in which $R^3$ is CH(=NOR$^x$) are obtained by reacting the aldehydes VI with the alkoxyamines VII under conditions known per se (Scheme 3).

Moreover, the aldehydes VI can be converted under conditions known per se with organometallic reagents, such as Grignard reagents VIII (R$^y$—Mg—X; X=Cl, Br, I), into the secondary alcohols IX.

The oxidation of these alcohols IX, preferably according to Swern using oxalyl chloride/DMSO, gives the ketones X which for their part can be reacted with alkoxyamines VII to give the compounds Ib according to the invention.

The active compounds Ic in which $R^3$ is cyano (Scheme 4) can preferably be prepared by reacting the aldehydes VI with hydroxylamine, followed by dehydration of the resulting oximes XI (similarly to EP-A 457 726).

Scheme 3

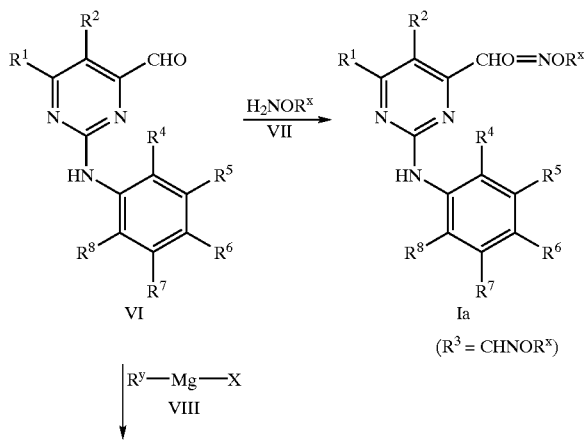

Scheme 4

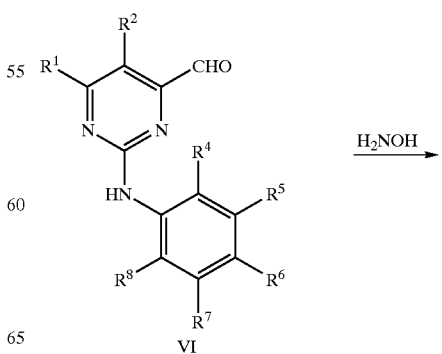

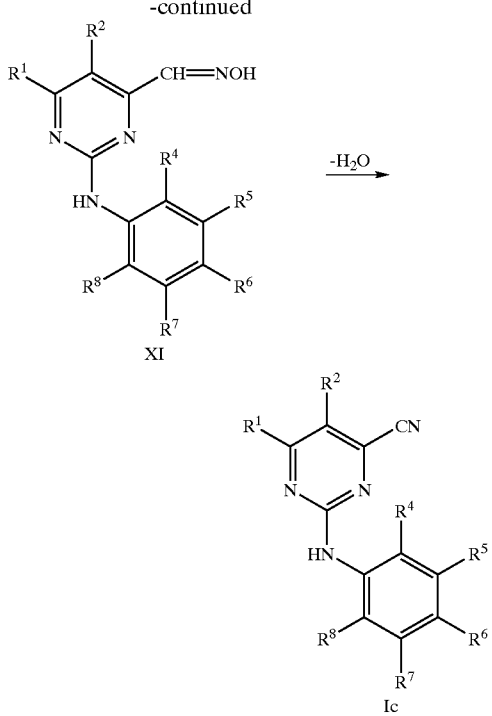

In the definition of the compounds I given at the outset, collective terms which represent individual enumerations of each of the group members were used for the radicals $R^1$ to $R^8$, $R^x$ and $R^y$ and $R^a$ and $R^b$. The radicals alkyl, alkoxy, alkoxycarbonyl, alkenyl and alkynyl can be straight-chain or branched.

Examples of meanings are:

halogen: fluorine, chlorine, bromine or iodine;

$C_1$–$C_4$-alkyl: methyl, ethyl, propyl, 1-methylethyl, butyl, 1-methylpropyl, 2-methylpropyl or 1,1-dimethylethyl;

$C_1$–$C_8$-alkyl: $C_1$–$C_4$-alkyl, as mentioned above, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl, 1-ethyl-3-methylpropyl, heptyl, octyl or 2-ethylhexyl;

$C_1$–$C_2$-haloalkyl: a $C_1$–$C_2$-alkyl radical as mentioned above which is partially or fully substituted by fluorine, chlorine, bromine and/or iodine, i.e. for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl;

$C_1$–$C_4$-alkoxy and the alkoxy moieties of $C_1$–$C_4$-alkoxycarbonyl: methoxy, ethoxy, propoxy, 1-methylethoxy, butoxy, 1-methylpropoxy, 2-methylpropoxy or 1,1-dimethylethoxy;

$C_1$–$C_2$-haloalkoxy: a $C_1$–$C_2$-alkoxy radical as mentioned above which is partially or fully substituted by fluorine, chlorine, bromine and/or iodine, i.e. for example fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy;

$C_2$–$C_6$-alkenyl: ethylene, prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl and 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_2$–$C_6$-alkynyl: ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl or 1-ethyl-1-methyl-2-propynyl;

$C_3$–$C_8$-cycloalkyl: cyclopropyl, cyclobutyl, cyclopentyl, cyclohexyl, cycloheptyl or cyclooctyl.

With a view to their use as fungicides, preference is given to 2-(N-phenylamino)pyrimidines I which have the following substituents, the preference existing in each case alone or in combination:

$R^1$, $R^3$ are cyano, $C_1$–$C_8$-alkyl, propynyl, $C_1$–$C_2$-haloalkyl, cyclopropyl or a group $C(=NOR^x)R^y$;

$R^2$ is halogen or $C_1$–$C_8$-alkyl;

$R^4$ to $R^8$ independently of one another are hydrogen, cyano, halogen, $C_1$–$C_2$-haloalkyl, $C_1$–$C_2$-haloalkoxy, $R^a$ or $R^aO$—$N$=$C(R^b)$;

$R^a$, $R^b$ are $C_1$–$C_4$-alkyl.

Particular preference is given to 2-(N-phenylamino) pyrimidines I having the following substituents, the preference existing in each case alone or in combination:

$R^1$, $R^3$ are cyano, methyl, ethyl, cyclopropyl, CH(=NOCH$_3$), CH(=NOC$_2$H$_5$), C(=NOCH$_3$)CH$_3$ or C(=NOC$_2$H$_5$)CH$_3$;

$R^2$ is fluorine, chlorine, methyl or ethyl;

$R^4$ to $R^8$ independently of one another are hydrogen, cyano, halogen or $C_1$–$C_4$-alkyl.

Most preference is given to 2-(N-phenylamino) pyrimidines I having the following substituents, the preference existing in each case alone or in combination.

$R^1$ is methyl or cyclopropyl;

$R^2$ is methyl or fluorine;

$R^3$ is CH(=NOCH$_3$), CH(=NOC$_2$H$_5$), C(=NOCH$_3$)CH$_3$, C(=NOC$_2$H$_5$)CH$_3$, cyano or methyl and $R^4$ to $R^8$ are hydrogen.

The following groups of active compounds are preferred owing to their pronounced plant-fungicidal activity.

Group Ia: 2-(N-phenylamino)pyrimidines of the formula I in which $R^1$, $R^3$ are cyano, $C_1$–$C_8$-alkyl, $C_2$–$C_6$-alkenyl, $C_2$–$C_6$-alkynyl or $C_3$–$C_8$-cycloalkyl;

$R^2$ is halogen, $C_1$–$C_8$-alkyl, $C_2$–$C_6$-alkenyl, $C_2$–$C_6$-alkynyl or $C_1$–$C_2$-haloalkyl;

$R^4$, $R^6$, $R^8$ independently of one another are hydrogen, cyano, halogen, $R^a$, $R^aO$, $R^aS(O)_m$, $R^aO$—(C=O), $R^a$(C=O), $R^aR^bN$—(C=O), $R^aHN$—(C=O), $H_2N$—(C=O), $R^a$—(C=O)—NH, $R^a$—(C=O)—NR$^b$ or $R^aO$—N=C(R$^b$);

$R^5$, $R^7$ independently of one another are hydrogen, cyano, $R^a$, $R^aO$, $R^aS(O)_m$, $R^aO$—(C=O), $R^a$(C=O), $R^aR^bN$—(C=O), $R^aHN$—(C=O), $H_2N$—(C=O), $R^a$—(C=O)—NH, $R^a$—(C=O)—NR$^b$ or $R^aO$—N=C(R$^b$);

$R^a$, $R^b$ are $C_1$–$C_4$-alkyl, $C_3$–$C_6$-alkenyl or $C_3$–$C_6$-alkynyl, each of which may be substituted by cyano, halogen, $C_1$–$C_4$-alkoxy, $C_1$–$C_4$-alkoxycarbonyl or phenyl, or are phenyl which may carry one to three substituents selected from the group consisting of halogen and $C_1$–$C_4$-alkyl, and m is 0, 1 or 2.

Preference is given to 2-(N-phenylamino)pyrimidines of the group Ia in which $R^1$ is cyano, methyl, ethyl, n-propyl, propynyl or cyclopropyl;

$R^2$ is methyl, ethyl, fluorine or chlorine;

$R^3$ is methyl;

$R^4$, $R^6$, $R^8$ independently of one another are hydrogen, cyano, halogen, $C_1$–$C_2$-haloalkoxy, $R^a$ or $R^aO$—N=C(R$^b$) and are preferably hydrogen, halogen or $C_1$–$C_4$-alkyl;

$R^5$, $R^7$ independently of one another are hydrogen, cyano, $C_1$–$C_2$-haloalkoxy, $R^a$ or $R^aO$—N=C(R$^b$) and are preferably hydrogen, halogen or $C_1$–$C_4$-alkyl and $R^a$, $R^b$ are $C_1$–$C_4$-alkyl.

Group Ib: 2-(N-phenylamino)pyrimidines of the formula I in which $R^1$ is cyano or $C_2$–$C_6$-alkynyl and the radicals $R^2$ to $R^8$ are each as defined in claim 1.

Preference is given to 2-(N-phenylamino)pyrimidines of the group Ib in which $R^1$ is cyano or propynyl;

$R^2$ is halogen or $C_1$–$C_8$-alkyl and is preferably fluorine, chlorine, methyl or ethyl;

$R^3$ is cyano, $C_1$–$C_8$-alkyl, propynyl, $C_1$–$C_2$-haloalkyl or cyclopropyl and is preferably methyl, ethyl, n-propyl, propynyl or cyclopropyl;

$R^4$ to $R^8$ independently of one another are hydrogen, cyano, halogen, $C_1$–$C_2$-haloalkyl, $C_1$–$C_2$-haloalkoxy, $R^a$ or $R^aO$—N=C(R$^b$) and are preferably hydrogen, halogen or $C_1$–$C_4$-alkyl and $R^a$, $R^b$ are $C_1$–$C_4$-alkyl.

Group Ic: 2-(N-phenylamino)pyrimidines of the formula I in which $R^4$ to $R^8$ are hydrogen and the radicals $R^1$ to $R^3$ are each as defined in claim 1.

Preference is given to 2-(N-phenylamino)pyrimidines of the group Ic in which $R^1$, $R^3$ are cyano, $C_1$–CB-alkyl, propynyl, $C_1$–$C_2$-haloalkyl or cyclopropyl and are preferably methyl, ethyl, n-propyl, propynyl or cyclopropyl;

$R^2$ is halogen or $C_1$–$C_8$-alkyl and is preferably fluorine, chlorine, methyl or ethyl and $R^4$ to $R^8$ are hydrogen.

Group Id: 2-(N-phenylamino)pyrimidines of the formula I in which $R^2$ is halogen;

$R^4$, $R^8$ independently of one another are hydrogen, cyano, halogen, $C_1$–$C_2$-haloalkoxy, $R^a$, $R^aO$, $R^aS(O)_m$, $R^aO$—(C=O), $R^a$(C=O), $R^aR^bN$—(C=O), $R^aHN$—(C=O), $H_2N$—(C=O), $R^a$—(C=O)—NH, $R^a$—(C=O)—NR$^b$ or $R^aO$—N=C(R$^b$);

$R^5$ to $R^7$ independently of one another are hydrogen, cyano, halogen, $C_1$–$C_2$-haloalkyl, $C_1$–$C_2$-haloalkoxy, $R^a$, $R^aO$, $R^aS(O)_m$, $R^aO$—(C=O), $R^a$(C=O), $R^aR^bN$—(C=O), $R^aHN$—(C=O), $H_2N$—(C=O), $R^a$—(C=O)—NH, $R^a$—(C=O)—NR$^b$ or $R^aO$—N=C(R$^b$);

$R^a$, $R^b$ are $C_1$–$C_4$-alkyl, $C_3$–$C_6$-alkenyl or $C_3$–$C_6$-alkynyl, each of which may be substituted by cyano, $C_1$–$C_4$-alkoxy, $C_1$–$C_4$-alkoxycarbonyl or phenyl, or are phenyl, which may carry one to three substituents selected from the group consisting of halogen and $C_1$–$C_4$-alkyl, and the radicals $R^1$ and $R^3$ are each as defined in claim 1.

Preference is given to 2-(N-phenylamino)pyrimidines of the group Id in which $R^1$, $R^3$ are cyano, $C_1$–$C_8$-alkyl, propynyl, $C_1$–$C_2$-haloalkyl or cyclopropyl and are preferably methyl, ethyl, n-propyl, propynyl or cyclopropyl;

$R^2$ is fluorine or chlorine;

$R^4$, $R^8$ independently of one another are hydrogen, cyano, halogen, $C_1$–$C_2$-haloalkoxy, $R^a$ or $R^aO$—N=C(R$^b$) and are preferably hydrogen, halogen or $C_1$–$C_4$-alkyl;

$R^5$ to $R^7$ independently of one another are hydrogen, cyano, halogen, $C_1$–$C_2$-haloalkyl, $C_1$–$C_2$-haloalkoxy, $R^a$ or $R^aO$—N=C(R$^b$) and are preferably hydrogen, halogen or $C_1$–$C_4$-alkyl and $R^a$, $R^b$ are $C_1$–$C_4$-alkyl.

Group Ie: 2-(N-phenylamino)pyrimidines of the formula I in which $R^1$, $R^3$ are $C_1$–$C_8$-alkyl, $C_2$–$C_6$-alkenyl or $C_2$–$C_6$-alkynyl, where the radicals alkenyl and alkynyl may be substituted by cyano, halogen, $C_1$–$C_4$-alkoxy or $C_1$–$C_4$-alkoxycarbonyl;

$R^2$ is $C_1$–$C_8$-alkyl, $C_2$–$C_6$-alkenyl or $C_2$–$C_6$-alkynyl;

$R^5$, $R^7$ independently of one another are hydrogen, cyano, $R^a$, $R^aO$, $R^aS(O)_m$, $R^aO$—(C=O), $R^a(C$=O), $R^aR^bN$—(C=O), $R^aHN$—(C=O), $H_2N$—(C=O), $R^a$—(C=O)—NH, $R^a$—(C=O)—$NR^b$ or $R^aO$—N=C($R^b$);

the radicals $R^4$, $R^6$ and $R^8$ are each as defined in claim 1.

Preference is given to 2-(N-phenylamino)pyrimidines of the group Ie in which $R^1$, $R^3$ are methyl, ethyl, n-propyl or propynyl;

$R^2$ is methyl, ethyl or n-propyl;

$R^4$, $R^6$, $R^8$ independently of one another are hydrogen, cyano, halogen, $C_1$–$C_2$-haloalkyl, $C_1$–$C_2$-haloalkoxy, $R^a$ or $R^aO$—N=C($R^b$) and are preferably hydrogen, halogen or $C_1$–$C_4$-alkyl;

$R^5$, $R^7$ independently of one another are hydrogen, cyano, $C_1$–$C_2$-haloalkyl, $C_1$–$C_2$-haloalkoxy, $R^a$ or $R^aO$—N=C($R^b$) and are preferably hydrogen, cyano, $C_1$–$C_4$-alkyl or $C_1$–$C_2$-haloalkyl and $R^a$, $R^b$ are $C_1$–$C_4$-alkyl.

Group If: 2-(N-phenylamino)pyrimidines of the formula I in which $R^4$, $R^8$ are hydrogen;

$R^5$, $R^7$ independently of one another are hydrogen, cyano, $C_1$–$C_2$-haloalkoxy, $R^a$, $R^aO$, $R^aS(O)_m$, $R^aO$—(C=O), $R^a(C$=O), $R^aR^bN$—(C=O), $R^aHN$—(C=O), $H_2N$—(C=O), $R^a$—(C=O)—NH, $R^a$—(C=O)—$NR^b$ or $R^aO$—N=C($R^b$);

$R^6$ is hydrogen, cyano, halogen, $C_1$–$C_2$-haloalkyl, $C_1$–$C_2$-haloalkoxy, $R^a$, $R^aO$, $R^aS(O)_m$, $R^aO$—(C=O), $R^a(C$=O), $R^aR^bN$—(C=O), $R^aHN$—(C=O), $H_2N$—(C=O), $R^a$—(C=O)—NH, $R^a$—(C=O)—$NR^b$ or $R^aO$—N=C($R^b$);

$R^a$, $R^b$ are $C_1$–$C_4$-alkyl, $C_3$–$C_6$-alkenyl or $C_3$–$C_6$-alkynyl, each of which may be substituted by cyano, $C_1$–$C_4$-alkoxy, $C_1$–$C_4$-alkoxycarbonyl or phenyl, or are phenyl which may carry one to three substituents selected from the group consisting of halogen and $C_1$–$C_4$-alkyl, and the radicals $R^1$ to $R^3$ are each as defined in claim 1.

Preference is given to 2-(N-phenylamino)pyrimidines of the group If in which $R^1$, $R^3$ are cyano, $C_1$–$C_8$-alkyl, propynyl, $C_1$–$C_2$-haloalkyl or cyclopropyl and are preferably methyl, ethyl, n-propyl, propynyl or cyclopropyl;

$R^2$ is halogen or $C_1$–$C_8$-alkyl and is preferably fluorine, chlorine, methyl or ethyl;

$R^4$, $R^8$ are hydrogen;

$R^5$, $R^7$ independently of one another are hydrogen, cyano, $C_1$–$C_2$-haloalkoxy, $R^a$ or $R^aO$—N=C($R^b$) and are preferably hydrogen, cyano, $R^a$ or $R^aO$—N=C($R^b$);

$R^6$ is hydrogen, cyano, halogen, $C_1$–$C_2$-haloalkyl, $C_1$–$C_2$-haloalkoxy, $R^a$ or $R^aO$—N=C($R^b$) and is preferably hydrogen, halogen or $C_1$–$C_4$-alkyl and $R^a$, $R^b$ are $C_1$–$C_4$-alkyl.

Group Ig: 2-(N-phenylamino)pyrimidines of the formula I in which $R^1$ is cyclopropyl;

$R^3$ is cyano, $C_1$–$C_8$-alkyl, $C_2$–$C_6$-alkenyl, $C_2$–$C_6$-alkynyl, where the radicals alkyl, alkenyl and alkynyl may be substituted by cyano, $C_1$–$C_4$-alkoxy or $C_1$–$C_4$-alkoxycarbonyl, or is $C_3$–$C_8$-cycloalkyl;

the radicals $R^2$ and $R^4$ to $R^8$ are each as defined in claim 1.

Preference is given to 2-(N-phenylamino)pyrimidines of the group Ig in which $R^1$ is cyclopropyl;

$R^2$ is halogen or $C_1$–$C_8$-alkyl and is preferably fluorine, chlorine, methyl or ethyl;

$R^3$ is cyano, $C_1$–$C_8$-alkyl, propynyl or cyclopropyl and is preferably methyl, ethyl, n-propyl, propynyl or cyclopropyl;

$R^4$ to $R^8$ independently of one another are hydrogen, cyano, halogen, $C_1$–$C_2$-haloalkyl, $C_1$–$C_2$-haloalkoxy, $R^a$ or $R^aO$—N=C($R^b$) and are preferably hydrogen, halogen or $C_1$–$C_4$-alkyl and $R^a$, $R^b$ are $C_1$–$C_4$-alkyl.

Examples of particularly preferred 2-(N-phenylamino)pyrimidines are compiled in the Tables below.

TABLE 1

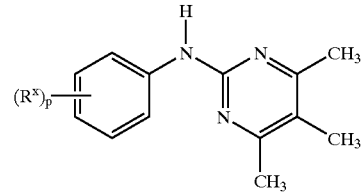

2-(N-phenylamino)pyrimidines I.1-001 to I.1-379 of the formula I.1.

| Number | $(R^x)_p$ |
|--------|-----------|
| 1 | H |
| 2 | 2-F |
| 3 | 4-F |
| 4 | 2,4-$F_2$ |
| 5 | 2,4,6-$F_3$ |
| 6 | 2,6-$F_2$ |
| 7 | 2-Cl |
| 8 | 4-Cl |
| 9 | 2,4-$Cl_2$ |
| 10 | 2,6-$Cl_2$ |
| 11 | 2,4,6-$Cl_3$ |
| 12 | 2-Br |
| 13 | 4-Br |
| 14 | 2,4-$Br_2$ |
| 15 | 2,6-$Br_2$ |
| 16 | 2,4,6-$Br_3$ |
| 17 | 2-I |
| 18 | 4-I |
| 19 | 2,4-$I_2$ |
| 20 | 2-Cl, 4-F |
| 21 | 2-Cl, 6-F |
| 22 | 2-Cl, 4-Br |
| 23 | 2-Cl, 6-Br |
| 24 | 2-Br, 4-Cl |
| 25 | 2-Br, 4-F |
| 26 | 2-Br, 6-F |
| 27 | 2-F, 4-Cl |
| 28 | 2,6-$Cl_2$, 4-Br |
| 29 | 2-$CH_3$ |
| 30 | 3-$CH_3$ |
| 31 | 4-$CH_3$ |
| 32 | 2,3-$(CH_3)_2$ |
| 33 | 2,4-$(CH_3)_2$ |
| 34 | 2,5-$(CH_3)_2$ |
| 35 | 2,6-$(CH_3)_2$ |
| 36 | 3,4-$(CH_3)_2$ |
| 37 | 3,5-$(CH_3)_2$ |

-continued

| Number | (R^x)_p |
|---|---|
| 38 | 2,3,5-(CH_3)_3 |
| 39 | 2,3,4-(CH_3)_3 |
| 40 | 2,3,6-(CH_3)_3 |
| 41 | 2,4,5-(CH_3)_3 |
| 42 | 2,4,6-(CH_3)_3 |
| 43 | 3,4,5-(CH_3)_3 |
| 44 | 2,3,4,6-(CH_3)_4 |
| 45 | 2,3,5,6-(CH_3)_4 |
| 46 | 2,3,4,5,6-(CH_3)_5 |
| 47 | 2-C_2H_5 |
| 48 | 3-C_2H_5 |
| 49 | 4-C_2H_5 |
| 50 | 2,4-(C_2H_5)_5 |
| 51 | 2,6-(C_2H_5)_2 |
| 52 | 3,5-(C_2H_5)_2 |
| 53 | 2,4,6-(C_2H_5)_3 |
| 54 | 2-n-C_3H_7 |
| 55 | 3-n-C_3H_7 |
| 56 | 4-n-C_3H_7 |
| 57 | 2-i-C_3H_7 |
| 58 | 3-i-C_3H_7 |
| 59 | 4-i-C_3H_7 |
| 60 | 2,4-(i-C_3H_7)_2 |
| 61 | 2,6-(i-C_3H_7)_2 |
| 62 | 3,5-(i-C_3H_7)_2 |
| 63 | 2-s-C_4H_9 |
| 64 | 3-s-C_4H_9 |
| 65 | 4-s-C_4H_9 |
| 66 | 2-t-C_4H_9 |
| 67 | 3-t-C_4H_9 |
| 68 | 4-t-C_4H_9 |
| 69 | 2-CH_3, 4-t-C_4H_9 |
| 70 | 2-CH_3, 6-t-C_4H_9 |
| 71 | 2-CH_3, 4-i-C_3H_7 |
| 72 | 2-CH_3, 5-i-C_3H_7 |
| 73 | 3-CH_3, 4-i-C_3H_7 |
| 74 | 2-Cl, 4-C_6H_5 |
| 75 | 2-Br, 4-C_6H_5 |
| 76 | 2-OCH_3 |
| 77 | 3-OCH_3 |
| 78 | 4-OCH_3 |
| 79 | 2-OC_2H_5 |
| 80 | 3-O—C_2H_5 |
| 81 | 4-O—C_2H_5 |
| 82 | 2-O-n-C_3H_7 |
| 83 | 3-O-n-C_3H_7 |
| 84 | 4-O-n-C_3H_7 |
| 85 | 2-O-i-C_3H_7 |
| 86 | 3-O-i-C_3H_7 |
| 87 | 4-O-i-C_3H_7 |
| 88 | 2-O-n-C_6H_{13} |
| 89 | 3-O-n-C_6H_{13} |
| 90 | 4-O-n-C_6H_{13} |
| 91 | 2-O—CH_2C_6H_5 |
| 92 | 3-O—CH_2C_6H_5 |
| 93 | 4-O—CH_2C_6H_5 |
| 94 | 2,3-(OCH_3)_2 |
| 95 | 2,4-(OCH_3)_2 |
| 96 | 2,5-(OCH_3)_2 |
| 97 | 2,6-(OCH_3)_2 |
| 98 | 3,4-(OCH_3)_2 |
| 99 | 3,5-(OCH_3)_2 |
| 100 | 2-O-t-C_4H_9 |
| 101 | 3-O-t-C_4H_9 |
| 102 | 4-O-t-C_4H_9 |
| 103 | 2-O-C_6H_5 |
| 104 | 3-O-C_6H_5 |
| 105 | 4-O-C_6H_5 |
| 106 | 2-O-(2'-F—C_6H_4) |
| 107 | 3-O-(3'-Cl—C_6H_4) |
| 108 | 4-O-(4'-CH_3—C_6H_4) |
| 109 | 2,3,6-(CH_3)_3, 4-F |
| 110 | 2,3,6-(CH_3)_3, 4-Cl |
| 111 | 2,3,6-(CH_3)_3, 4-Br |
| 112 | 2-i-C_3H_7, 4-Cl, 5-CH_3 |
| 113 | 2-CH_3, 5-i-C_3H_7, 4-Cl |
| 114 | 2-CH_2—OCH_3 |
| 115 | 3-CH_2—OCH_3 |
| 116 | 4-CH_2—OCH_3 |
| 117 | 2-C_6H_5 |
| 118 | 3-C_6H_5 |
| 119 | 4-C_6H_5 |
| 120 | 2-(2'-F—C_6H_4) |
| 121 | 2-(3'-F—C_6H_4) |
| 122 | 2-(4'-F—C_6H_4) |
| 123 | 3-(2'-F—C_6H_4) |
| 124 | 3-(3'-F—C_6H_4) |
| 125 | 3-(4'-F—C_6H_4) |
| 126 | 4-(2'-F—C_6H_4) |
| 127 | 4-(3'-F—C_6H_4) |
| 128 | 4-(4'-F—C_6H_4) |
| 129 | 3-(3'-Cl—C_6H_4) |
| 130 | 4-(4'-CH_3—C_6H_4) |
| 131 | 2-CF_3 |
| 132 | 3-CF_3 |
| 133 | 4-CF_3 |
| 134 | 2-OCF_3 |
| 135 | 3-OCF_3 |
| 136 | 4-OCF_3 |
| 137 | 3-OCH_2CHF_2 |
| 138 | 2-CN |
| 139 | 3-CN |
| 140 | 4-CN |
| 141 | 2-F, 3-CH_3 |
| 142 | 2-F, 4-CH_3 |
| 143 | 2-F, 5-CH_3 |
| 144 | 2-F, 6-CH_3 |
| 145 | 2-Cl, 3-CH_3 |
| 146 | 2-Cl, 4-CH_3 |
| 147 | 2-Cl, 5-CH_3 |
| 148 | 2-Cl, 6-CH_3 |
| 149 | 2-Br, 3-CH_3 |
| 150 | 2-Br, 4-CH_3 |
| 151 | 2-Br, 5-CH_3 |
| 152 | 2-Br, 6-CH_3 |
| 153 | 4-F, 2-CH_3 |
| 154 | 4-F, 3-CH_3 |
| 155 | 4-Cl, 2-CH_3 |
| 156 | 4-Cl, 3-CH_3 |
| 157 | 4-Br, 2-CH_3 |
| 158 | 4-Br, 3-CH_3 |
| 159 | 2-F, 3,5-(CH_3)_2 |
| 160 | 2-F, 3,4-(CH_3)_2 |
| 161 | 2-F, 3,6-(CH_3)_2 |
| 162 | 2-F, 4,5-(CH_3)_2 |
| 163 | 2-F, 4,6-(CH_3)_2 |
| 164 | 2-F, 5,6-(CH_3)_2 |
| 165 | 2-Cl, 3,5-(CH_3)_2 |
| 166 | 2-Cl, 3,4-(CH_3)_2 |
| 167 | 2-Cl, 3,6-(CH_3)_2 |
| 168 | 2-Cl, 4,5-(CH_3)_2 |
| 169 | 2-Cl, 4,6-(CH_3)_2 |
| 170 | 2-Cl, 5,6-(CH_3)_2 |
| 171 | 2-Br, 3,5-(CH_3)_2 |
| 172 | 2-Br, 3,4-(CH_3)_2 |
| 173 | 2-Br, 3,6-(CH_3)_2 |
| 174 | 2-Br, 4,5-(CH_3)_2 |
| 175 | 2-Br, 4,6-(CH_3)_2 |
| 176 | 2-Br, 5,6-(CH_3)_2 |
| 177 | 4-F, 2,3-(CH_3)_2 |
| 178 | 4-F, 2,5-(CH_3)_2 |
| 179 | 4-F, 2,6-(CH_3)_2 |
| 180 | 4-F, 3,5-(CH_3)_2 |
| 181 | 4-F, 3,6-(CH_3)_2 |
| 182 | 4-Cl, 2,3-(CH_3)_2 |
| 183 | 4-Cl, 2,5-(CH_3)_2 |
| 184 | 4-Cl, 2,6-(CH_3)_2 |
| 185 | 4-Cl, 3,5-(CH_3)_2 |
| 186 | 4-Cl, 3,6-(CH_3)_2 |
| 187 | 4-Br, 2,3-(CH_3)_2 |
| 188 | 4-Br, 2,5-(CH_3)_2 |
| 189 | 4-Br, 2,6-(CH_3)_2 |
| 190 | 4-Br, 3,5-(CH_3)_2 |
| 191 | 4-Br, 3,6-(CH_3)_2 |

-continued

| Number | $(R^x)_p$ |
|---|---|
| 192 | 2,4-$F_2$, 3-$CH_3$ |
| 193 | 2,4-$F_2$, 5-$CH_3$ |
| 194 | 2,4-$F_2$, 6-$CH_3$ |
| 195 | 2,6-$F_2$, 3-$CH_3$ |
| 196 | 2,6-$F_2$, 4-$CH_3$ |
| 197 | 2,4-$Cl_2$, 3-$CH_3$ |
| 198 | 2,4-$Cl_2$, 5-$CH_3$ |
| 199 | 2,4-$Cl_2$, 6-$CH_3$ |
| 200 | 2,6-$Cl_2$, 3-$CH_3$ |
| 201 | 2,6-$Cl_2$, 4-$CH_3$ |
| 202 | 2,4-$Br_2$, 3-$CH_3$ |
| 203 | 2,4-$Br_2$, 5-$CH_3$ |
| 204 | 2,4-$Br_2$, 6-$CH_3$ |
| 205 | 2,6-$Br_2$, 3-$CH_3$ |
| 206 | 2,6-$Br_2$, 4-$CH_3$ |
| 207 | 2-$SCH_3$ |
| 208 | 3-$SCH_3$ |
| 209 | 4-$SCH_3$ |
| 210 | 2-$SOCH_3$ |
| 211 | 3-$SOCH_3$ |
| 212 | 4-$SOCH_3$ |
| 213 | 2-$SO_2CH_3$ |
| 214 | 3-$SO_2CH_3$ |
| 215 | 4-$SO_2CH_3$ |
| 216 | 2-$CO_2CH_3$ |
| 217 | 3-$CO_2CH_3$ |
| 218 | 4-$CO_2CH_3$ |
| 219 | 2-$CO_2C_2H_5$ |
| 220 | 3-$CO_2C_2H_5$ |
| 221 | 4-$CO_2C_2H_5$ |
| 222 | 2-$CO_2$-n-$C_3H_7$ |
| 223 | 3-$CO_2$-n-$C_3H_7$ |
| 224 | 4-$CO_2$-n-$C_3H_7$ |
| 225 | 2-$CO_2$-i-$C_3H_7$ |
| 226 | 3-$CO_2$-i-$C_3H_7$ |
| 227 | 4-$CO_2$-i-$C_3H_7$ |
| 228 | 2-$CO_2$-t-$C_4H_9$ |
| 229 | 3-$CO_2$-t-$C_4H_9$ |
| 230 | 4-$CO_2$-t-$C_4H_9$ |
| 231 | 2-$COCH_3$ |
| 232 | 3-$COCH_3$ |
| 233 | 4-$COCH_3$ |
| 234 | 2-$COC_2H_5$ |
| 235 | 3-$COC_2H_5$ |
| 236 | 4-$COC_2H_5$ |
| 237 | 2-CO-n-$C_3H_7$ |
| 238 | 3-CO-n-$C_3H_7$ |
| 239 | 4-CO-n-$C_3H_7$ |
| 240 | 2-CO-i-$C_3H_7$ |
| 241 | 3-CO-i-$C_3H_7$ |
| 242 | 4-CO-i-$C_3H_7$ |
| 243 | 2-$CH_3$, 4-$COCH_3$ |
| 244 | 2,5-$(CH_3)_2$, 4-$COCH_3$ |
| 245 | 2-Cl, 4-$COCH_3$ |
| 246 | 2-C(=$NOCH_3$)—$CH_3$ |
| 247 | 3-C(=$NOCH_3$)—$CH_3$ |
| 248 | 4-C(=$NOCH_3$)—$CH_3$ |
| 249 | 2-C(=$NOC_2H_5$)—$CH_3$ |
| 250 | 3-C(=$NOC_2H_5$)—$CH_3$ |
| 251 | 4-C(=$NOC_2H_5$)—$CH_3$ |
| 252 | 2-C(=NO-n-$C_3H_7$)—$CH_3$ |
| 253 | 3-C(=NO-n-$C_3H_7$)—$CH_3$ |
| 254 | 4-C(=NO-n-$C_3H_7$)—$CH_3$ |
| 255 | 2-C(=NO-i-$C_3H_7$)—$CH_3$ |
| 256 | 3-C(=NO-i-$C_3H_7$)—$CH_3$ |
| 257 | 4-C(=NO-i-$C_3H_7$)—$CH_3$ |
| 258 | 2-C(=NO-allyl)-$CH_3$ |
| 259 | 3-C(=NO-allyl)-$CH_3$ |
| 260 | 4-C(=NO-allyl)-$CH_3$ |
| 261 | 2-C(=NO-trans-Cl-allyl)-$CH_3$ |
| 262 | 3-C(=NO-trans-Cl-allyl)-$CH_3$ |
| 263 | 4-C(=NO-trans-Cl-allyl)-$CH_3$ |
| 264 | 2-C(=NO-propargyl)-$CH_3$ |
| 265 | 3-C(=NO-propargyl)-$CH_3$ |
| 266 | 4-C(=NO-propargyl)-$CH_3$ |
| 267 | 2,5-$(CH_3)_2$, 4-C(=$NOCH_3$)—$CH_3$ |
| 268 | 2-Cl, 5-$CH_3$, 4-C(=$NOCH_3$)—$CH_3$ |
| 269 | 2-CO—$NH_2$ |
| 270 | 3-CO—$NH_2$ |
| 271 | 4-CO—$NH_2$ |
| 272 | 2-CO—$NHCH_3$ |
| 273 | 3-CO—$NHCH_3$ |
| 274 | 4-CO—$NHCH_3$ |
| 275 | 2-CO—$NHC_2H_5$ |
| 276 | 3-CO—$NHC_2H_5$ |
| 277 | 4-CO—$NHC_2H_5$ |
| 278 | 2-CO—NH-t-$C_4H_9$ |
| 279 | 3-CO—NH-t-$C_4H_9$ |
| 280 | 4-CO—NH-t-$C_4H_9$ |
| 281 | 2-CO—NH-allyl |
| 282 | 3-CO—NH-allyl |
| 283 | 4-CO—NH-allyl |
| 284 | 2-CO—NH-propargyl |
| 285 | 3-CO—NH-propargyl |
| 286 | 4-CO—NH-propargyl |
| 287 | 2-CO—NH—($CH_2C_6H_5$) |
| 288 | 3-CO—NH—($CH_2C_6H_5$) |
| 289 | 4-CO—NH—($CH_2C_6H_5$) |
| 290 | 2-CO—N($CH_3$)$_2$ |
| 291 | 3-CO—N($CH_3$)$_2$ |
| 292 | 4-CO—N($CH_3$)$_2$ |
| 293 | 2-CO—N($C_2H_5$)$_2$ |
| 294 | 3-CO—N($C_2H_5$)$_2$ |
| 295 | 4-CO—N($C_2H_5$)$_2$ |
| 296 | 2-CO—N(n-$C_3H_7$)$_2$ |
| 297 | 3-CO—N(n-$C_3H_7$)$_2$ |
| 298 | 4-CO—N(n-$C_3H_7$)$_2$ |
| 299 | 2-CO—N(i-$C_3H_7$)$_2$ |
| 300 | 3-CO—N(i-$C_3H_7$)$_2$ |
| 301 | 4-CO—N(i-$C_3H_7$)$_2$ |
| 302 | 2-CO—N(t-$C_4H_9$)$_2$ |
| 303 | 3-CO—N(t-$C_4H_9$)$_2$ |
| 304 | 4-CO—N(t-$C_4H_9$)$_2$ |
| 305 | 2-CO—N($CH_3$)$CH_2C_6H_5$ |
| 306 | 3-CO—N($CH_3$)$CH_2C_6H_5$ |
| 307 | 4-CO—N($CH_3$)$CH_2C_6H_5$ |
| 308 | 2-CO—N($CH_3$)$C_2H_5$ |
| 309 | 3-CO—N($CH_3$)$C_2H_5$ |
| 310 | 4-CO—N($CH_3$)$C_2H_5$ |
| 311 | 2-CO—N($CH_3$)n-$C_3H_7$ |
| 312 | 3-CO—N($CH_3$)n-$C_3H_7$ |
| 313 | 4-CO—N($CH_3$)n-$C_3H_7$ |
| 314 | 2-CO—N($CH_3$)i-$C_3H_7$ |
| 315 | 3-CO—N($CH_3$)i-$C_3H_7$ |
| 316 | 4-CO—N($CH_3$)i-$C_3H_7$ |
| 317 | 2-CO—N($CH_3$)t-$C_4H_9$ |
| 318 | 3-CO—N($CH_3$)t-$C_4H_9$ |
| 319 | 4-CO—N($CH_3$)t-$C_4H_9$ |
| 320 | 2-CO—N($CH_3$)allyl |
| 321 | 3-CO—N($CH_3$)allyl |
| 322 | 4-CO—N($CH_3$)allyl |
| 323 | 2-CO—N($CH_3$)propargyl |
| 324 | 3-CO—N($CH_3$)propargyl |
| 325 | 4-CO—N($CH_3$)propargyl |
| 326 | 2-NH—CO—$CH_3$ |
| 327 | 3-NH—CO—$CH_3$ |
| 328 | 4-NH—CO—$CH_3$ |
| 329 | 2-NH—CO—$C_2H_5$ |
| 330 | 3-NH—CO—$C_2H_5$ |
| 331 | 4-NH—CO—$C_2H_5$ |
| 332 | 2-NH—CO-n-$C_3H_7$ |
| 333 | 3-NH—CO-n-$C_3H_7$ |
| 334 | 4-NH—CO-n-$C_3H_7$ |
| 335 | 2-NH—CO-t-$C_4H_9$ |
| 336 | 3-NH—CO-t-$C_4H_9$ |
| 337 | 4-NH—CO-t-$C_4H_9$ |
| 338 | 2-NH—CO—CH=CH—$CH_3$ |
| 339 | 3-NH—CO—CH=CH—$CH_3$ |
| 340 | 4-NH—CO—CH=CH—$CH_3$ |
| 341 | 2-NH—CO—$C_6H_5$ |
| 342 | 3-NH—CO—$C_6H_5$ |
| 343 | 4-NH—CO—$C_6H_5$ |
| 344 | 2-N($CH_3$)—CO—$CH_3$ |
| 345 | 3-N($CH_3$)—CO—$CH_3$ |

-continued

| Number | $(R^x)_p$ |
|---|---|
| 346 | 4-N(CH$_3$)—CO—CH$_3$ |
| 347 | 2-N(CH$_3$)—CO—C$_2$H$_5$ |
| 348 | 3-N(CH$_3$)—CO—C$_2$H$_5$ |
| 349 | 4-N(CH$_3$)—CO—C$_2$H$_5$ |
| 350 | 2-N(CH$_3$)—CO-n-C$_3$H$_7$ |
| 351 | 3-N(CH$_3$)—CO-n-C$_3$H$_7$ |
| 352 | 4-N(CH$_3$)—CO-n-C$_3$H$_7$ |
| 353 | 2-N(CH$_3$)—CO-i-C$_3$H$_7$ |
| 354 | 3-N(CH$_3$)—CO-i-C$_3$H$_7$ |
| 355 | 4-N(CH$_3$)—CO-i-C$_3$H$_7$ |
| 356 | 2-N(CH$_3$)—CO-t-C$_4$H$_9$ |
| 357 | 3-N(CH$_3$)—CO-t-C$_4$H$_9$ |
| 358 | 4-N(CH$_3$)—CO-t-C$_4$H$_9$ |
| 359 | 2-N(CH$_3$)—CO—CH=CH—CH$_3$ |
| 360 | 3-N(CH$_3$)—CO—CH=CH—CH$_3$ |
| 361 | 4-N(CH$_3$)—CO—CH=CH—CH$_3$ |
| 362 | 2-N(CH$_3$)—CO—C$_6$H$_5$ |
| 363 | 3-N(CH$_3$)—CO—C$_6$H$_5$ |
| 364 | 4-N(CH$_3$)—CO—C$_6$H$_5$ |
| 365 | 2-N(C$_2$H$_5$)—CO—CH$_3$ |
| 366 | 3-N(C$_2$H$_5$)—CO—CH$_3$ |
| 367 | 4-N(C$_2$H$_5$)—CO—CH$_3$ |
| 368 | 2-N(n-C$_3$H$_7$)—CO—CH$_3$ |
| 369 | 3-N(n-C$_3$H$_7$)—CO—CH$_3$ |
| 370 | 4-N(n-C$_3$H$_7$)—CO—CH$_3$ |
| 371 | 2-N(i-C$_3$H$_7$)—CO—CH$_3$ |
| 372 | 3-N(i-C$_3$H$_7$)—CO—CH$_3$ |
| 373 | 4-N(i-C$_3$H$_7$)—CO—CH$_3$ |
| 374 | 2-N(t-C$_4$H$_9$)—CO—CH$_3$ |
| 375 | 3-N(t-C$_4$H$_9$)—CO—CH$_3$ |
| 376 | 4-N(t-C$_4$H$_9$)—CO—CH$_3$ |
| 377 | 2-N(CH$_2$C$_6$H$_5$)—CO—CH$_3$ |
| 378 | 3-N(CH$_2$C$_6$H$_5$)—CO—CH$_3$ |
| 379 | 4-N(CH$_2$C$_6$H$_5$)—CO—CH$_3$ |

TABLE 2

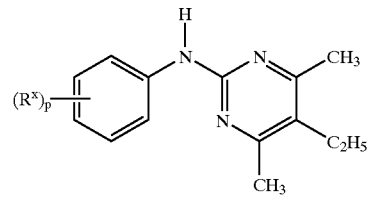

I.2

2-(N-phenylamino)pyrimidines I.2-001 to I.2-379 of the formula I.2, in which the meaning of $(R^x)_p$ is given by the rows of Table 1.

TABLE 3

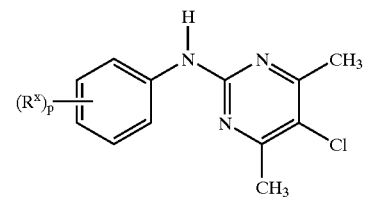

I.3

2-(N-phenylamino)pyrimidines I.3-001 to I.3-379 of the formula I.3, in which the meaning of $(R^x)_p$ is given by the rows of Table 1.

TABLE 4

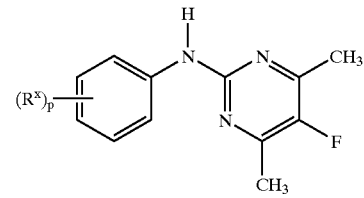

I.4

2-(N-phenylamino)pyrimidines I.4-001 to I.4-379 of the formula I.4, in which the meaning of $(R^x)_p$ is given by the rows of Table 1.

TABLE 5

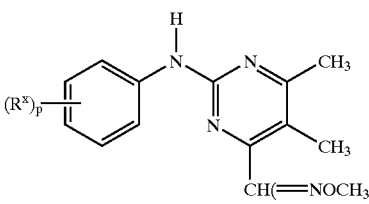

I.5

2-(N-phenylamino)pyrimidines I.5-001 to I.5-379 of the formula I.5, in which the meaning of $(R^x)_p$ is given by the rows of Table 1.

TABLE 6

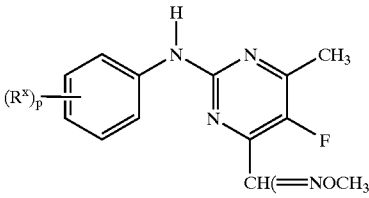

I.6

2-(N-phenylamino)pyrimidines I.6-001 to I.6-379 of the formula I.6, in which the meaning of $(R^x)_p$ is given by the rows of Table 1.

TABLE 7

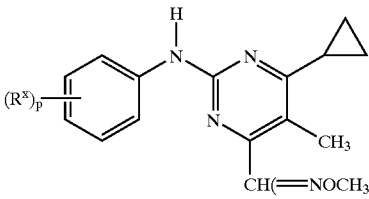

I.7

2-(N-phenylamino)pyrimidines I.7-001 to I.7-379 of the formula I.7, in which the meaning of $(R^x)_p$ is given by the rows of Table 1.

TABLE 8

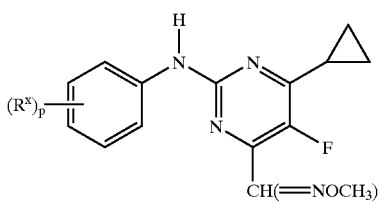

I.8

2-(N-phenylamino)pyrimidines I.8-001 to I.8-379 of the formula I.8, in which the meaning of $(R^x)_p$ is given by the rows of Table 1.

TABLE 9

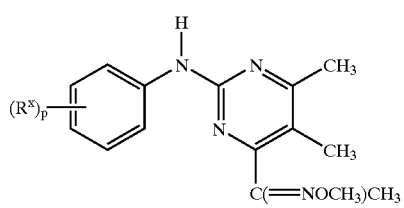

I.9

2-(N-phenylamino)pyrimidines I.9-001 to I.9-379 of the formula I.9, in which the meaning of $(R^x)_p$ is given by the rows of Table 1.

TABLE 10

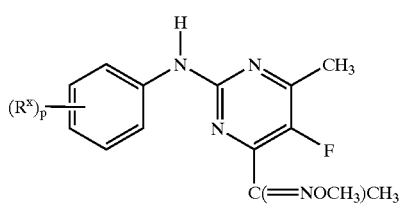

I.10

2-(N-phenylamino)pyrimidines I.10-001 to I.10-379 of the formula I.10, in which the meaning of $(R^x)_p$ is given by the rows of Table 1.

TABLE 11

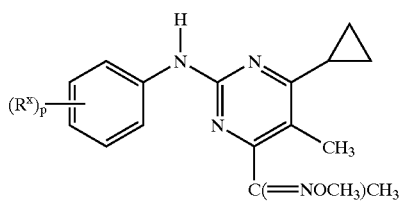

I.11

2-(N-phenylamino)pyrimidines I.11-001 to I.11-379 of the formula I.11, in which the meaning of $(R^x)_p$ is given by the rows of Table 1.

TABLE 12

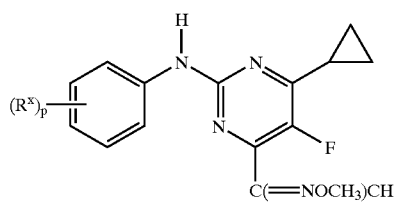

I.12

2-(N-phenylamino)pyrimidines I.12-001 to I.12-379 of the formula I.12, in which the meaning of $(R^x)_p$ is given by the rows of Table 1.

TABLE 13

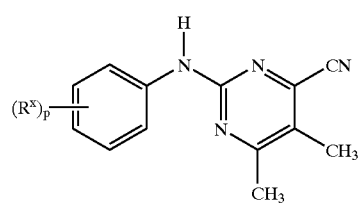

I.13

2-(N-phenylamino)pyrimidines I.13-001 to I.13-379 of the formula I.13, in which the meaning of $(R^x)_p$ is given by the rows of Table 1.

TABLE 14

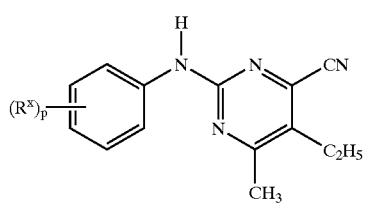

I.14

2-(N-phenylamino)pyrimidines I.14-001 to I.14-379 of the formula I.14, in which the meaning of $(R^x)_p$ is given by the rows of Table 1.

TABLE 15

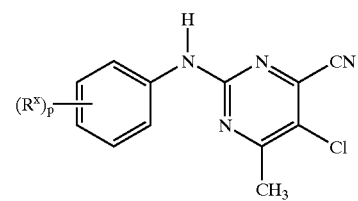

I.15

2-(N-phenylamino)pyrimidines I.15-001 to I.15-379 of the formula I.15, in which the meaning of $(R^x)_p$ is given by the rows of Table 1.

TABLE 16

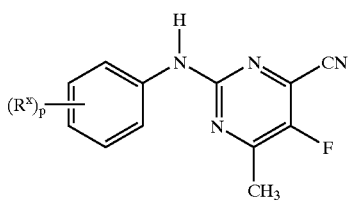
I.16

2-(N-phenylamino)pyrimidines I.16-001 to I.16-379 of the formula I.16, in which the meaning of $(R^x)_p$ is given by the rows of Table 1.

TABLE 17

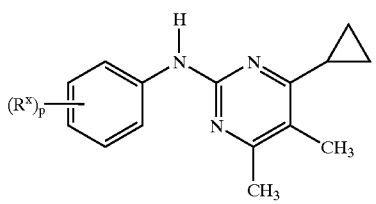
I.17

2-(N-phenylamino)pyrimidines I.17-001 to I.17-379 of the formula I.17, in which the meaning of $(R^x)_p$ is given by the rows of Table 1.

TABLE 18

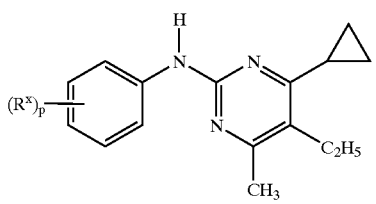
I.18

2-(N-phenylamino)pyrimidines I.18-001 to I.18-379 of the formula I.18, in which the meaning of $(R^x)_p$ is given by the rows of Table 1.

TABLE 19

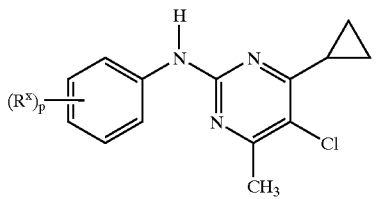
I.19

2-(N-phenylamino)pyrimidines I.19-001 to I.19-379 of the formula I.19, in which the meaning of $(R^x)_p$ is given by the rows of Table 1.

TABLE 20

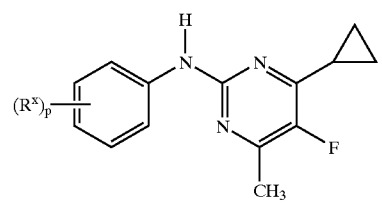
I.20

2-(N-phenylamino)pyrimidines I.20-001 to I.20-379 of the formula I.20, in which the meaning of $(R^x)_p$ is given by the rows of Table 1.

TABLE 21

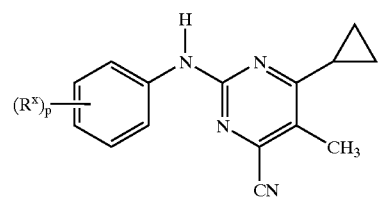
I.21

2-(N-phenylamino)pyrimidines I.21-001 to I.21-379 of the formula I.21, in which the meaning of $(R^x)_p$ is given by the rows of Table 1.

TABLE 22

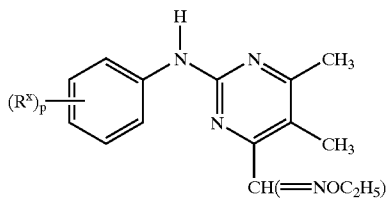
I.22

2-(N-phenylamino)pyrimidines I.22-001 to I.22-379 of the formula I.22, in which the meaning of $(R^x)_p$ is given by the rows of Table 1.

TABLE 23

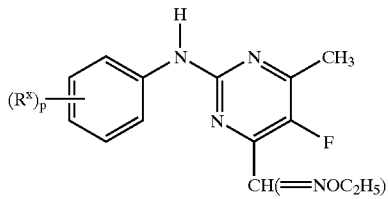
I.23

2-(N-phenylamino)pyrimidines I.23-001 to I.23-379 of the formula I.23, in which the meaning of $(R^x)_p$ is given by the rows of Table 1.

TABLE 24

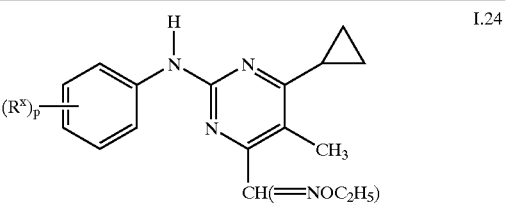

2-(N-phenylamino)pyrimidines I.24-001 to I.24-379 of the formula I.24, in which the meaning of $(R^x)_p$ is given by the rows of Table 1.

TABLE 25

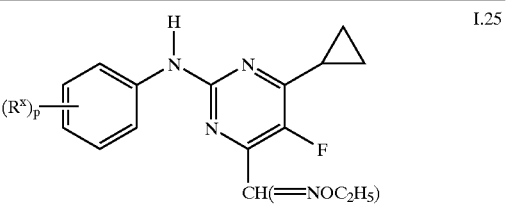

2-(N-phenylamino)pyrimidines I.25-001 to I.25-379 of the formula I.25, in which the meaning of $(R^x)_p$ is given by the rows of Table 1.

The compounds I are suitable for use as fungicides. They have outstanding activity against a broad spectrum of phytopathogenic fungi, in particular from the classes of the Ascomycetes, Deuteromycetes, Phycomycetes and Basidiomycetes. Some of them act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

Alternaria species on vegetables and fruit,
*Botrytis cinerea* (gray mold) on strawberries, vegetables, ornamentals and grapevines,
*Cercospora arachidicola* on peanuts,
*Erysiphe cichoracearum* and *Sphaerotheca fuliginea* on cucurbits,
*Erysiphe graminis* (powdery mildew) on cereals,
Fusarium and Verticillium species on various plants,
Helminthosporium species on cereals,
Mycosphaerella species on bananas and peanuts,
*Phytophthora infestans* on potatoes and tomatoes,
*Plasmopara viticola* on grapevines,
*Podosphaera leucotricha* on apples,
*Pseudocercosporella herpotrichoides* on wheat and barley,
Pseudoperonospora species on hops and cucumbers,
Puccinia species on cereals,
*Pyricularia oryzae* on rice,
Rhizoctonia species on cotton, rice and turf,
*Septoria nodorum* on wheat,
*Uncinula necator* on grapevines,
Ustilago species on cereals and sugar cane, and
Venturia species (scab) on apples and pears.

Moreover, the compounds I are suitable for controlling harmful fungi such as *Paecilomyces variotii* in the protection of materials (e.g. wood, paper, paint dispersions, fibers and fabrics) and in the protection of stored products.

The compounds I are applied by treating the fungi, or the plants, seeds, materials or the soil to be protected against fungal infection, with a fungicidally active amount of the active ingredients. Application can be effected both before and after infection of the materials, plants or seeds by the fungi.

In general, the fungicidal compositions comprise from 0.1 to 95, preferably 0.5 to 90, % by weight of active ingredient.

When used in crop protection, the rates of application are from 0.01 to 2.0 kg of active ingredient per ha, depending on the nature of the desired effect.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the desired effect. Rates of application conventionally used in the protection of materials are, for example, from 0.001 g to 2 kg, preferably 0.005 g to 1 kg, of active ingredient per cubic meter of material treated.

The compounds I can be converted into the customary formulations, e.g. solutions, emulsions, suspensions, dusts, powders, pastes and granules. The use form depends on the particular purpose; it is intended to ensure in each case a fine and uniform distribution of the compound according to the invention.

The formulations are prepared in a known manner, e.g. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. highly disperse silica, silicates); emulsifiers such as nonionic and anionic emulsifiers (e.g. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol and formaldehyde, polyoxyethylene octylphenyl ether, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone and water.

Powders, materials for spreading and dusts can be prepared by mixing or concomitantly grinding the active substances with a solid carrier.

Granules, e.g. coated granules, impregnated granules and homogeneous granules, can be prepared by binding the active ingredients to solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

The following are examples of formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, e.g. in the form of directly sprayable solutions, powders, suspensions or dispersions, emulsions, oil dispersions, pastes, dusts, materials for spreading, or granules, by means of spraying, atomizing, dusting, spreading or pouring. The use forms depend entirely on the intended purposes; it is intended to ensure in each case the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

Various types of oils, herbicides, fungicides, other pesticides, or bactericides may be added to the active ingredients, if appropriate just immediately prior to use (tank mix). These agents can be admixed with the agents according to the invention in a weight ratio of 1:10 to 10:1.

In the use form as fungicides, the compositions according to the invention can also be present together with other active ingredients, e.g. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl)disulfide;

nitro derivatives, such as dinitro(1-methylheptyl)phenyl crotonate, 2-sec-butyl-4,6-dinitrophenyl-3,3-dimethylacrylate, 2-sec-butyl-4,6-dinitrophenylisopropyl carbonate, diisopropyl 5-nitroisophthalate;

heterocyclic substances, such as 2-heptadecyl-2-imidazoline 45 acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]-quinoxaline, methyl 1-(butylcarbamoyl)-2-benzimidazolecarbamate, 2-methoxycarbonylaminobenzimidazole, 2-(2-furyl)benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide;

N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, cyclohexyl 2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS, 3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene; strobilurins such as methyl E-methoxyimino-[α-(o-tolyloxy)-o-tolyl]acetate, methyl E-2-{2-[6-(2-cyanophenoxy)pyrimidin-4-yloxy]-phenyl}-3-methoxyacrylate, methyl-E-methoxyimino-[α-(2-phenoxyphenyl)]acetamide, methyl-E-methoxyimino-[α-(2,5-dimethylphenoxy)-o-tolyl]acetamide;

anilinopyrimidines such as N-(4,6-dimethylpyrimidin-2-yl)aniline, N-[4-methyl-6-(1-propynyl)pyrimidin-2-yl]aniline, N-[4-methyl-6-cyclopropylpyrimidin-2-yl]aniline;

phenylpyrroles such as 4-(2,2-difluoro-1,3-benzodioxol-4-yl)pyrrole-3-carbonitrile;

cinnamamides such as 3-(4-chlorophenyl)-3-(3,4-dimethoxyphenyl)acryloylmorpholine;

and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-amino-butyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoro-methyl-3-chloro-2-aminopyridine, 1-((bis(4-fluorophenyl)methylsilyl)methyl)-1H-1,2,4-triazole.

SYNTHESIS EXAMPLES

With due modification of the starting compounds, the protocols shown in the synthesis examples below were used for obtaining further compounds I. The resulting compounds, together with physical data, are listed in the Tables which follow.

1. 4,6-Dimethyl-5-ethyl-2-(N-phenylamino)pyrimidine

A mixture of 5.5 g (42 mmol) of 3-ethylacetylacetone and 6 g (30 mmol) of phenylguanidinium hydrogencarbonate was heated at 100° C. for approximately 3 hours, during which a slight vacuum (200 mbar) was applied. The reaction mixture was subsequently cooled to room temperature and taken up in methylene chloride. The organic phase was extracted with water, dried over magnesium sulfate and concentrated. The residue was purified by column chromatography using cyclohexane/ethyl acetate mixtures. This gives 2.1 g (31%) of the title compound as a clear solid.

$^1$H-NMR (CDCl$_3$; δ in ppm): 7.65 (d, 2H); 7.35 (s,broad, 1H); 7.3 (t, 2H); 6.95 (t, 1H); 2.55 (q, 2H); 2.4 (s, 6H); 1.1 (t, 3H).

2. 5,6-Dimethyl-4-(N-methoxyimino)methyl-2-(N-phenylamino)pyrimidine

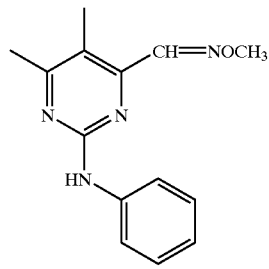

a) 1,1-Diethoxy-3-methylpentane-2,4-dione

At 0° C., a solution of 43 g (0.22 mol) of 1,1-diethoxypentane-2,4-dione in 400 ml of methylene chloride was admixed with 60 g (0.38 mol) of methyl iodide and 36 g (0.23 mol) of diazabicycloundecene (DBU).

The mixture was then stirred at room temperature for about 3 hours. An additional 20 g (0.13 mol) of DBU were then added, and the mixture was stirred at room temperature overnight.

The reaction mixture was then extracted with water, dilute hydrochloric acid (pH=1) and water, dried over magnesium sulfate and concentrated. 44 g of a yellow oil which, according to DC and $^1$H-NMR, contained about 50% of the title compound, 40% of 1,1-diethoxy-3,3-dimethylpentane-2,4-dione and about 3% of 1,1-diethoxypentane-2,4-dione were obtained as residue.

The resulting crude product was used in the next reaction without further purification.

$^1$H-NMR (CDCl$_3$, δ in ppm): 4.65 (s, 1H); 4.05 (q, 1H); 3.7 (m, 4H); 2.25 (s, 3H); 1.2 (m, 9H).

b) 5,6-Dimethyl-4-diethoxymethyl-2-(phenylamino)pyrimidine

A mixture of 44 g (purity about 50%, about 0.11 mol) of 1,1-diethoxy-3-methylpentane-2,4-dione (crude product, Example 2a) and 35 g (0.175 mol) of phenylguanidinium bicarbonate in 300 ml of ethanol was heated at 70–80° C. for about 3 hours. The reaction mixture was then concentrated and the residue was filtered, with suction, through silica gel using methyl tert-butyl ether. The solvent was evaporated. Less volatile components were distilled off under a pressure of 0.3 mbar, at a bath temperature of 150° C. The residue obtained was 38 g (quantitative yield) of the title compound as a yellow oil.

$^1$H-NMR (CDCl$_3$, δ in ppm): 7.7 (d, 2H); 7.3 (t, 2H); 7.1 (s, broad, 1H); 7.0 (t, 1H); 5.35 (s, 1H); 3.75 (m, 2H); 3.6 (m, 2H); 2.45 (s, 3H); 2.25 (s, 3H); 1.25 (t, 6H).

c) 5,6-Dimethyl-4-formyl-2-(phenylamino)pyrimidine

A mixture of 38 g (0.126 mol) of 5,6-dimethyl-4-diethoxymethyl-2-(phenylamino)pyrimidine (Example 2b) and 50 ml of conc. hydrochloric acid in 400 ml of water was heated at 60° C. for about 3 hours.

The reaction mixture was then cooled, resulting in the precipitation of a solid. The reaction mixture was adjusted to pH=6 using dilute aqueous sodium hydroxide solution, and the precipitated solid was filtered off with suction. The solid was then washed with acetone and dried at a pressure of about 100 mbar and a temperature of 50° C. for 48 hours. This gave 29 g (quantitative yield) of the title compound as a yellow solid.

$^1$H-NMR (DMSO-d$_6$, δ in ppm): 9.95 (s, 1H); 9.75 (s, broad, 1H); 7.8 (d, 2H); 7.3 (t, 2H); 6.95 (t, 1H); 2.5, (s, 3H); 2.3 (s, 3H).

d) 5,6-Dimethyl-4-(N-methoxyimino)methyl-2-(phenylamino)pyrimidine

A mixture of 1.1 g (5 mmol) of 5,6-dimethyl-4-formyl-2-(phenylamino)pyrimidine (Example 2c) and 0.5 g (6 mmol) of O-methylhydroxylamine hydrochloride in 20 ml of methanol was refluxed for about 1 hour.

The reaction mixture was then concentrated using a rotary evaporator. The residue was taken up in methylene chloride and the organic phase was extracted with NaHCO$_3$ solution. The solvent was evaporated and the residue was purified by column chromatography using cyclohexane/methyl t-butyl ether mixtures. This gave 0.8 g (3.1 mmol, 63%) of the title compound as a yellow solid (m.p.=85–88° C.).

$^1$H-NMR (CDCl$_3$, δ in ppm): 8.2 (s, 1H); 7.65 (d, 2H); 7.3 (t, 2H); 7.1 (s, broad, 1H); 7.0 (t, 1H); 4.05 (s, 3H); 2.5 (s, 3H); 2.3 (s, 3H).

3. 4-Cyano-5,6-dimethyl-2-(phenylamino)pyrimidine

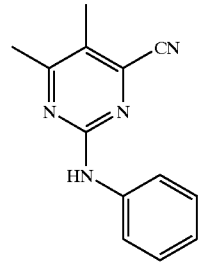

A mixture of 2.5 g (11 mmol) of 5,6-dimethyl-4-formyl-2-phenylaminopyrimidine (Example 2c) and 1.2 g (17 mmol) of hydroxylamine hydrochloride in 10 ml of pyridine was heated at 50° C. for about 1.5 hours.

3.5 ml (37 mmol) of acetic anhydride were then added dropwise, and the reaction mixture was stirred at 90° C. for about 1.5 hours. The reaction mixture was then concentrated using a rotary evaporator. The residue was diluted with water and adjusted to pH 7–8 using dilute aqueous sodium hydroxide solution. The aqueous phase was extracted with ethyl acetate and methylene chloride. The combined organic phases were then filtered, with suction, through silica gel and the silica gel was washed with methylene chloride/ethyl acetate 2:1. The organic phase was then concentrated. The residue crystallized and was triturated with diisopropyl ether. This gave 1.9 g (75%) of the title compound as a pale solid (m.p.=181–184° C.).

$^1$H-NMR (CDCl$_3$, δ in ppm): 7.6 (d, 2H); 7.35 (t, 2H); 7.15 (s, broad, 1H); 7.05 (t, 1H); 2.5 (s, 3H); 2.35 (s, 3H).

TABLE A (Compounds I including phys. data)

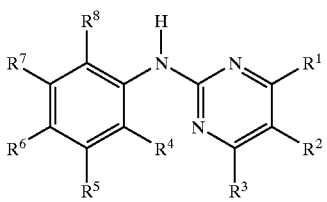

| Ex. | R¹ | R² | R³ | R⁴ | R⁵ | R⁶ | R⁷ | R⁸ | m.p. (° C.), IR (cm⁻¹) or ¹H—NMR (ppm) |
|---|---|---|---|---|---|---|---|---|---|
| I.01 | CH₃ | C₂H₅ | CH₃ | H | H | H | H | H | 79–83 |
| I.02 | cyclo-propyl | C₂H₅ | CH₃ | H | H | H | H | H | resin |
| I.03 | CH₃ | CH₃ | CH₃ | H | H | H | H | H | 132–135 |
| I.04 | cyclo-propyl | CH₃ | CH₃ | H | H | H | H | H | 76–79 |
| I.05 | CH₃ | Cl | CH₃ | H | H | H | H | H | 100–102 |
| I.06 | cyclo-propyl | Cl | CH₃ | H | H | H | H | H | 98–100 |
| I.07 | CH₃ | F | CH₃ | H | H | H | H | H | 89–93 |
| I.08 | cyclo-propyl | F | CH₃ | H | H | H | H | H | 95–97 |
| I.09 | CH₃ | CH₃ | CN | H | H | H | H | H | 181–184 |
| I.10 | CH₃ | C₂H₅ | CN | H | H | H | H | H | 1597, 1578, 1559, 1527, 1498, 1445, 1427, 1343, 1317, 749 |
| I.11 | i-C₃H₇ | CH₃ | CN | H | H | H | H | H | 149–153 |
| I.12 | i-C₃H₇ | C₂H₅ | CN | H | H | H | H | H | 3332, 1600, 1573, 1532, 1500, 1487, 1448, 1429, 1532, 761 |
| I.13 | cyclo-propyl | CH₃ | CN | H | H | H | H | H | 3339, 1600, 1579, 1561, 1531, 1498, 1447, 1426, 1240, 746 |
| I.14 | cyclo-propyl | C₂H₅ | CN | H | H | H | H | H | 3323, 1603, 1575, 1533, 1500, 1485, 1446, 1429, 1352, 753 |
| I.15 | C₂H₅ | CH₃ | CN | H | H | H | H | H | 3357, 1600, 1578, 1563, 1520, 1498, 1462, 1445, 1430, 755 |
| I.16 | cyclo-propyl | CH₃ | CH₃ | Br | H | H | H | H | 118–120 |
| I.17 | cyclo-propyl | CH₃ | CH₃ | H | H | Br | H | H | 96–98 |
| I.18 | CH₃ | CH₃ | CF₃ | H | H | H | H | H | 105–108 |
| I.19 | CH₃ | CH₃ | vinyl | H | H | H | H | H | 110–112 |
| I.20 | CH₃ | CH₃ | cis-propenyl-1 | H | H | H | H | H | 86–89 |
| I.21 | CH₃ | CH₃ | 2-CH₃-propenyl-1 | H | H | H | H | H | 75–101 |
| I.22 | cyclo-propyl | CH₃ | vinyl | H | H | H | H | H | 98–101 |
| I.23 | cyclo-propyl | CH₃ | cis-propenyl-1 | H | H | H | H | H | 79–81 |
| I.24 | cyclo-propyl | CH₃ | trans-propenyl-1 | H | H | H | H | H | 76–78 |
| I.25 | cyclo-propyl | CH₃ | 2-CH₃-propenyl-1 | H | H | H | H | H | 79–84 |
| I.26 | cyclo-propyl | CH₃ | CH₃ | F | H | H | H | H | 1622, 1593, 1568, 1532, 1479, 1448, 1438, 1415, 1252, 749 |
| I.27 | cyclo-propyl | CH₃ | CH₃ | H | F | H | H | H | 80–82 |
| I.28 | cyclo-propyl | CH₃ | CH₃ | H | H | F | H | H | 119–120 |
| I.29 | cyclo-propyl | CH₃ | CH₃ | Cl | H | H | H | H | 95–96 |
| I.30 | cyclo-propyl | CH₃ | CH₃ | H | Cl | H | H | H | 108–110 |
| I.31 | cyclo-propyl | CH₃ | CH₃ | H | H | Cl | H | H | 110–111 |
| I.32 | cyclo-propyl | CH₃ | CH₃ | CH₃ | H | H | H | H | 126–128 |
| I.33 | cyclo-propyl | CH₃ | CH₃ | H | CH₃ | H | H | H | 81–83 |

TABLE A-continued (Compounds I including phys. data)

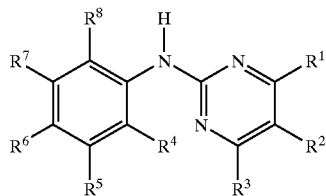

| Ex. | R¹ | R² | R³ | R⁴ | R⁵ | R⁶ | R⁷ | R⁸ | m.p. (° C.), IR (cm⁻¹) or ¹H—NMR (ppm) |
|---|---|---|---|---|---|---|---|---|---|
| I.34 | cyclo-propyl | CH₃ | CH₃ | H | H | CH₃ | H | H | 91–93 |
| I.35 | cyclo-propyl | CH₃ | CN | F | H | H | H | H | 172–174 |
| I.36 | cyclo-propyl | CH₃ | CN | H | F | H | H | H | 188–190 |
| I.37 | cyclo-propyl | CH₃ | CN | H | H | F | H | H | 167–169 |
| I.38 | cyclo-propyl | CH₃ | CN | Cl | H | H | H | H | 161–162 |
| I.39 | cyclo-propyl | CH₃ | CN | H | Cl | H | H | H | 193–194 |
| I.40 | cyclo-propyl | CH₃ | CN | H | H | Cl | H | H | 177–179 |
| I.41 | cyclo-propyl | CH₃ | CN | CH₃ | H | H | H | H | 148–150 |
| I.42 | cyclo-propyl | CH₃ | CN | H | CH₃ | H | H | H | 160–161 |
| I.43 | cyclo-propyl | CH₃ | CN | H | H | CH₃ | H | H | 174–176 |
| I.44 | CH₃ | CH₃ | CH₃ | F | H | H | H | H | 94 |
| I.45 | CH₃ | CH₃ | CH₃ | H | F | H | H | H | 167 |
| I.46 | CH₃ | CH₃ | CH₃ | H | H | F | H | H | 126 |
| I.47 | CH₃ | CH₃ | CH₃ | CH₃ | H | H | H | H | 95 |
| I.48 | CH₃ | CH₃ | CH₃ | H | CH₃ | H | H | H | 169–170 |
| I.49 | CH₃ | CH₃ | CH₃ | H | H | CH₃ | H | H | 171–174 |
| I.50 | CH₃ | CH₃ | CH₃ | Cl | H | H | H | H | 100–103 |
| I.51 | CH₃ | CH₃ | CH₃ | H | Cl | H | H | H | 177 |
| I.52 | CH₃ | CH₃ | CH₃ | H | H | Cl | H | H | 151–154 |
| I.53 | CH₃ | CH₃ | CN | F | H | H | H | H | 173–175 |
| I.54 | CH₃ | CH₃ | CN | H | F | H | H | H | 185–186 |
| I.55 | CH₃ | CH₃ | CN | H | H | F | H | H | 168–170 |
| I.56 | CH₃ | CH₃ | CN | CH₃ | H | H | H | H | 169–170 |
| I.57 | CH₃ | CH₃ | CN | H | CH₃ | H | H | H | 177–179 |
| I.58 | CH₃ | CH₃ | CN | H | H | CH₃ | H | H | 176–179 |
| I.59 | CH₃ | CH₃ | CN | Cl | H | H | H | H | 175–176 |
| I.60 | CH₃ | CH₃ | CN | H | Cl | H | H | H | 154–156 |
| I.61 | CH₃ | CH₃ | CN | H | H | Cl | H | H | 182–184 |
| I.62 | CH₃ | CH₃ | CH(=NOCH₃) | H | H | H | H | H | 85–88 |
| I.63 | CH₃ | CH₃ | CH(=NOC₂H₅) | H | H | H | H | H | 78–80 |
| I.64 | CH₃ | CH₃ | CH(=NO-i-C₃H₇) | H | H | H | H | H | 64–66 |
| I.65 | CH₃ | CH₃ | CH(=NOCH₂—C₆H₅) | H | H | H | H | H | 76–79 |
| I.66 | cyclo-propyl | CH₃ | CH(=NOCH₃) | H | H | H | H | H | 93–96 |
| I.67 | cyclo-propyl | CH₃ | CH(=NOC₂H₅) | H | H | H | H | H | 90–91 |
| I.68 | cyclo-propyl | CH₃ | CH(=NO-i-C₃H₇) | H | H | H | H | H | 100–104 |
| I.69 | cyclo-propyl | CH₃ | CH(=NOCH₂—C₆H₅) | H | H | H | H | H | 1602, 1594, 1560, 1523, 1497, 1444, 1409, 1012, 751, 696 |
| I.70 | cyclo-propyl | CH₃ | CH(=NOH) | H | H | H | H | H | 184–186 |

TABLE A-continued (Compounds I including phys. data)

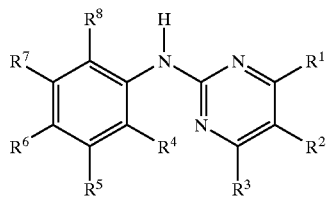

| Ex. | R¹ | R² | R³ | R⁴ | R⁵ | R⁶ | R⁷ | R⁸ | m.p. (° C.), IR (cm⁻¹) or ¹H—NMR (ppm) |
|---|---|---|---|---|---|---|---|---|---|
| I.71 | CH₃ | CH₃ | C(CH₃)=NOCH₃ nonpolar isomer | H | H | H | H | H | 2936, 1603, 1564, 1525, 1497, 1444, 1392, 1351, 1259, 1055, 915, 866, 790, 750, 691 |
| I.72 | CH₃ | CH₃ | C(CH₃)=NOCH₃ polar isomer | H | H | H | H | H | 148–150 |
| I.73 | CH₃ | CH₃ | C(CH₃)=NOC₂H₅ nonpolar isomer | H | H | H | H | H | 2977, 2931, 1603, 1564, 1525, 1498, 1444, 1388, 1353, 1258, 1052, 945, 930, 750, 691 |
| I.74 | CH₃ | CH₃ | C(CH₃)=NOC₂H₅ polar isomer | H | H | H | H | H | 116–118 |
| I.75 | CH₃ | CH₃ | C(CH₃)=NO-i-C₃H₇ nonpolar isomer | H | H | H | H | H | 2974, 1603, 1564, 1525, 1498, 1444, 1391, 1381, 1369, 1351, 1121, 1000, 956, 750, 691 |
| I.76 | CH₃ | CH₃ | C(CH₃)=NOCH₂—C₆H₅ isomer mixture | H | H | H | H | H | 1603, 1595, 1566, 1524, 1497, 1444, 1391, 1364, 1351, 1257, 1055, 1035, 1014, 751, 695 |
| I.77 | cyclo-propyl | CH₃ | C(CH₃)=NOCH₃ nonpolar isomer | H | H | H | H | H | 63–65 |
| I.78 | cyclo-propyl | CH₃ | C(CH₃)=NOC₂H₅ nonpolar isomer | H | H | H | H | H | 55–57 |
| I.79 | cyclo-propyl | CH₃ | C(CH₃)=NO-i-C₃H₇ nonpolar isomer | H | H | H | H | H | 1606, 1593, 1568, 1527, 1496, 1443, 1425, 1379, 1368, 1358, 1004, 963, 898, 747, 690 |
| I.80 | cyclo-propyl | CH₃ | C(CH₃)=NOCH₂—C₆H₅ nonpolar isomer | H | H | H | H | H | 1604, 1593, 1559, 1523, 1497, 1444, 1419, 1383, 1354, 1041, 1013, 903, 880, 750, 692 |
| I.81 | cyclo-propyl | CH₃ | C(CH₃)=NOCH₂—C₆H₅ polar isomer | H | H | H | H | H | 71–73 |
| I.82 | CH₃ | CH₃ | C(CH₃)=NO-i-C₃H₇ polar isomer | H | H | H | H | H | 2974, 1603, 1568, 1525, 1498, 1444, 1390, 1381, 1369, 1350, 1121, 1031, 955, 750, 691 |
| I.83 | cyclo-propyl | CH₃ | C(CH₃)=NOCH₃ polar isomer | H | H | H | H | H | 120–122 |
| I.84 | cyclo-propyl | CH₃ | C(CH₃)=NOC₂H₅ polar isomer | H | H | H | H | H | 115–117 |
| I.85 | cyclo-propyl | CH₃ | C(CH₃)=NO-i-C₃H₇ polar isomer | H | H | H | H | H | 98–102 |

Examples of the Action Against Harmful Fungi

The fungicidal action of the compounds of the formula I was demonstrated by the following experiments:

The active ingredients were formulated separately or jointly as a 10% emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Wettol® EM (nonionic emulsifier based on ethoxylated castor oil) and diluted with water to give the desired concentration.

The comparative compounds used were:
a) active compound A known from EP-A 457 726 (Table 1, No. 1.1)

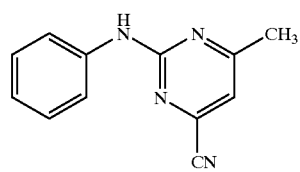

b) active compound B (is within the scope of the claims of EP-A 270 111)

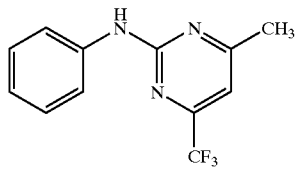

c) active compound C, known from JP 03-271 278 (Table 1, No. 2)

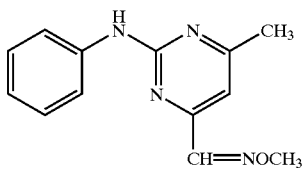

Comparative Experiment 1—Activity Against *Plasmopara viticola*

Leaves of potted grapevines c.v. "Müller-Thurgau" were sprayed to runoff point with an aqueous 500 ppm preparation of active compound which had been made up from a stock solution comprising 10% of active compound, 63% of cyclohexanone and 27% of emulsifier. To assess the persistency of the substances, the plants were kept for 7 days in a greenhouse after the spray-coating had dried off. Only then were the leaves inoculated with an aqueous zoospore suspension of *Plasmopara viticola*. The grapevines were then initially kept in a water vapor-saturated chamber at 24° C. for 48 hours and then in a greenhouse at 20–30° C. for 5 days. After this period of time, the plants were once more kept in a humid chamber for 16 hours to promote sporangiophore eruption. The extent of the infection on the undersides of the leaves was then determined visually.

In this test, the plants which had been treated with the active compound I.9 according to the invention showed an infection of 5%, while the plants which had been treated with the known active compound A were 50% infected and the untreated plants 85% infected.

Comparative Experiment 2—Curative Activity Against *Puccinia recondita* on Wheat (Wheat Leaf Rust)

Leaves of potted wheat seedlings c.v. "Kanzler" were dusted with spores of wheat leaf rust (*Puccinia recondita*). Thereafter, the pots were kept in a chamber of high atmospheric humidity (90 to 95%), at 20 to 22° C. for 24 hours. During this time, the spores germinated and the germ tubes penetrated into the leaf tissue. The next day, the infected plants were sprayed to runoff point with an aqueous 250 ppm preparation of active compound which had been made up from a stock solution consisting of 10% of active compound, 63% of cyclohexanone and 27% of emulsifier. After the spraycoating had dried on, the test plants were cultivated in a greenhouse at 20–22° C. and 65–70% relative atmospheric humidity for 7 days. The extent of the rust fungus development on the leaves was then determined.

In this test, the plants which had been treated with the active compound I.9 according to the invention showed an infection of 30%, while the plants which had been treated with the known active compound A and the untreated plants were 100% infected.

Comparative Experiment 3—Activity against *Pyricularia oryzae* (Protective)

Leaves of potted rice seedlings c.v. "TaiNong 67" were sprayed to runoff point with an aqueous 250 ppm preparation of active compound which had been made up from a stock solution comprising 10% of active compound, 63% of cyclohexanone and 27% of emulsifier. The next day, the plants were inoculated with an aqueous spore suspension of *Pyricularia oryzae*. The test plants were subsequently kept in conditioning chambers at 22–24° C. and 95–99% relative atmospheric humidity for 6 days. The extent of the development of the disease on the leaves was then determined visually.

In this test, the plants which had been treated with the active compound I.18 according to the invention showed an infection of 15%, while the plants which had been treated with the known active compound B were 80% infected and the untreated plants were 90% infected.

Comparative Experiment 4—Activity Against *Plasmopara viticola*

Leaves of potted grapevines c.v. "Müller-Thurgau" were sprayed to runoff point with an aqueous 250 ppm preparation of active compound which had been made up from a stock solution comprising 10% of active compound, 63% of cyclohexanone and 27% of emulsifier. To assess the persistency of the substances, the plants were kept for 7 days in a greenhouse after the spray-coating had dried off. Only then were the leaves inoculated with an aqueous zoospore suspension of *Plasmopara viticola*. The grapevines were then initially kept in a water vapor-saturated chamber at 24° C. for 48 hours and then in a greenhouse at 20–30° C. for 5 days. After this period of time, the plants were once more kept in a humid chamber for 16 hours to promote sporangiophore eruption. The extent of the infection on the undersides of the leaves was then determined visually.

In this test, the plants which had been treated with the active compound I.62 according to the invention showed an infection of 10%, while the plants which had been treated with the known active compound C were 60% infected and the untreated plants 85% infected.

We claim:
1. A 2-(N-phenylamino)pyrimidine of the formula I

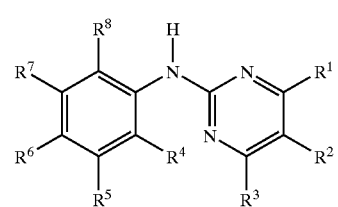

in which
$R^1$, $R^3$ independently of one another are cyano, $C_1$–$C_8$-alkyl, $C_2$–$C_6$-alkenyl, $C_2$–$C_6$-alkynyl or $C_3$–$C_8$-cycloalkyl or a group $C(=NOR^x)R^y$;
$R^x$ is hydrogen or $C_1$–$C_8$-alkyl;
$R^y$ is hydrogen or $C_1$–$C_8$-alkyl;
$R^2$ is halogen, $C_1$–$C_8$-alkyl, $C_2$–$C_6$-alkenyl, $C_2$–$C_6$-alkynyl or $C_1$–$C_2$-haloalkyl;
$R^4$ to $R^8$ independently of one another are hydrogen or halogen, which 2-(n-phenylamino)pyrimidine is fungicidally useful.

2. A 2-(N-phenylamino)pyrimidine of the formula I as claimed in claim 1, wherein $R^1$ is methyl or cyclopropyl.

3. A 2-(N-phenylamino)pyrimidine of the formula I as claimed in claim 1, wherein $R^4$ to $R^8$ are hydrogen.

4. A 2-(N-phenylamino)pyrimidine of the formula I as claimed in claim 1, wherein $R^2$ is halogen or methyl.

5. A 2-(N-phenylamino)pyrimidine of the formula I as claimed in claim 1, wherein $R^3$ is $CH(=NOCH_3)$, $CH(=NOC_2H_5)$, $C(=NOCH_3)CH_3$, $C(=NOC_2H_5)CH_3$, cyano or methyl.

6. A 2-(N-phenylamino)pyrimidine of the formula I

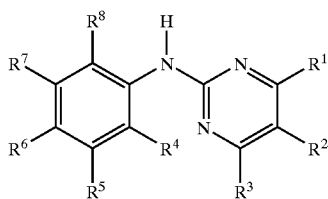

I in which
$R^1$ is methyl or cyclopropyl;
$R^2$ is halogen or methyl;
$R^3$ is trifluoromethyl;
$R^4$ to $R^8$ are hydrogen;
which 2-(n-phenylamino)pyrimidine is fungicidally useful.

7. The method of controlling harmful fungi by treating the fungi or the plants, seeds, material or the soil to be protected against fungal infection with a fungicidally effective amount of at least one 2-(N-phenylamino)pyrimidines of the formula I,

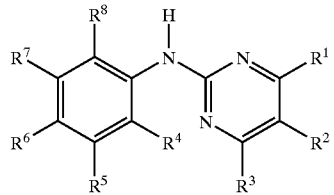

I where:

$R^1$, $R^3$ independently of one another are cyano, $C_1-C_8$-alkyl, $C_2-C_6$-alkenyl, $C_2-C_6$-alkynyl, where the radicals alkyl, alkenyl and alkynyl may be substituted by cyano, halogen, $C_1-C_4$-alkoxy or $C_1-C_4$-alkoxycarbonyl, or are $C_3-C_8$-cycloalkyl or a group $C(=NOR^x)R^y$;

$R^x$ is hydrogen, $C_1-C_8$-alkyl, $C_2-C_6$-alkenyl, $C_2-C_6$-alkynyl, where the radicals alkyl, alkenyl and alkynyl may be substituted by cyano, halogen, $C_1-C_4$-alkoxy or phenyl;

$R^y$ is hydrogen, $C_1-C_8$-alkyl, $C_2-C_6$-alkenyl, $C_2-C_6$-alkynyl, where the radicals alkyl, alkenyl and alkynyl may be substituted by cyano, halogen or $C_1-C_4$-alkoxy;

$R^2$ is halogen, $C_1-C_8$-alkyl, $C_2-C_6$-alkenyl, $C_2-C_6$-alkynyl, where the radicals alkyl, alkenyl and alkynyl may be substituted by cyano, halogen, $C_1-C_4$-alkoxy or $C_1-C_4$-alkoxycarbonyl;

$R^4$ to $R^8$ independently of one another are hydrogen or halogen.

* * * * *